(12) United States Patent
Giannotti et al.

(10) Patent No.: US 11,925,393 B2
(45) Date of Patent: Mar. 12, 2024

(54) PEDICLE SCREW RASP SYSTEM AND ADJUSTER

(71) Applicant: K2M, Inc., Leesburg, VA (US)

(72) Inventors: Geni Giannotti, Ridgewood, NJ (US); David Nuckley, Glen Rock, NJ (US); Carlos Sanchez, Butler, NJ (US)

(73) Assignee: K2M, Inc., Leesburg, VA (US)

( * ) Notice: Subject to any disclaimer, the term of this patent is extended or adjusted under 35 U.S.C. 154(b) by 262 days.

(21) Appl. No.: 16/912,933

(22) Filed: Jun. 26, 2020

(65) Prior Publication Data

US 2020/0405360 A1    Dec. 31, 2020

Related U.S. Application Data

(60) Provisional application No. 62/868,122, filed on Jun. 28, 2019.

(51) Int. Cl.
*A61B 17/70* (2006.01)
*A61B 17/16* (2006.01)
*A61B 17/17* (2006.01)

(52) U.S. Cl.
CPC ...... *A61B 17/7082* (2013.01); *A61B 17/1633* (2013.01); *A61B 17/1735* (2013.01)

(58) Field of Classification Search
CPC ............ A61B 17/7082; A61B 17/1633; A61B 17/1735; A61B 17/1659; A61B 17/1671; A61B 17/1604; A61B 17/1637; A61B 17/7091; A61B 17/7076; A61B 17/7086; A61B 17/3468; B23C 2210/246; B23C 2210/54; B23C 2210/24; B23B 51/0417; B23B 51/04; B23B 51/0466; B23B 2251/46
USPC ................ 30/299, 304, 305, 130, 113.1
See application file for complete search history.

(56) References Cited

U.S. PATENT DOCUMENTS

| | | | |
|---|---|---|---|
| 6,197,033 B1* | 3/2001 | Haid, Jr. | A61B 17/1757 606/279 |
| 7,018,418 B2* | 3/2006 | Amrich | B32B 3/30 623/23.74 |
| 8,029,539 B2* | 10/2011 | Kirschman | A61B 17/7032 606/246 |
| 8,123,751 B2* | 2/2012 | Shluzas | A61B 17/7002 606/279 |
| 9,097,067 B2* | 8/2015 | Gosamo | B28D 1/041 |
| 9,801,667 B2* | 10/2017 | Hawkes | A61B 17/7086 |
| 9,895,169 B2* | 2/2018 | Faulhaber | A61B 17/7035 |
| 9,999,451 B2* | 6/2018 | Biedermann | A61B 17/7076 |
| 10,058,360 B2 | 8/2018 | Fischer et al. | |
| 2005/0090829 A1* | 4/2005 | Martz | A61B 17/1604 606/167 |
| 2006/0036254 A1 | 2/2006 | Lim | |
| 2011/0184469 A1* | 7/2011 | Ballard | A61B 17/7086 606/279 |
| 2012/0203291 A1 | 8/2012 | Boulaine | |
| 2016/0262809 A1* | 9/2016 | May | A61B 17/7082 |
| 2018/0125559 A1* | 5/2018 | Ortiz | A61B 17/861 |

* cited by examiner

*Primary Examiner* — Tracy L Kamikawa
(74) *Attorney, Agent, or Firm* — Lerner David LLP

(57) ABSTRACT

A tulip rasp comprising a body, a handle adjacent a proximal end of the body, a head adjacent a distal end of the body, the head having at least one extension, each of which has a cutting edge, and a receiving space defined by the at least one extension.

22 Claims, 11 Drawing Sheets

PEDICLE SCREW RASP SYSTEM AND ADJUSTER

The present application claims the benefit of the filing date of U.S. Provisional Patent Application No. 62/868,122 filed Jun. 28, 2019, the disclosure of which is hereby incorporated herein by reference.

BACKGROUND OF THE INVENTION

Although spinal surgeries are largely designed to be a permanent solution to issues involving the spine, there may be times where such surgeries require revision. For example, revision spinal surgery may be required where the symptoms necessitating the initial spinal surgery may flare up again, the implants used with the initial spinal surgery malfunction, the portions of the spine surrounding the implant begin to deteriorate, or the portions of the spine on which surgery was performed show no signs of undergoing sufficient fusion.

In some instances, revision spinal surgeries may require an adjustment or replacement of a head of a pedicle screw (often referred to as a tulip or coupling element) implanted during the initial spinal surgery. In these cases, the surrounding tissue may have grown over and/or around the tulip head, thereby obstructing the surgeon's access to the tulip head during surgery. Although removing the surrounding tissue is possible, doing so may be difficult, especially in cases where the revision spinal surgery is done in a minimally invasive fashion. Additionally, removing the surrounding tissue must be done with care as it is the surgeon's goal to preserve as much of the patient's tissue as possible.

In some cases, a tulip head may be at an angle that requires adjusting after access to the tulip head has been acquired, or where access is limited as a result of the odd angle of the tulip head. Currently, there are no available tools specifically designed to engage and adjust the tulip head. To adjust tulip heads, surgeons presently use any available instruments at hand (e.g. plyers, screwdrivers, cobbs wrenches, rongeurs, or the like), even if they are not directed specifically towards a spinal surgery. However, such tools are not designed with the specific purpose of adjusting tulip heads in mind, and, therefore, are inefficient. For instance, plyers require a certain level of grip and dexterity that a surgeon may find difficult to provide in light of fluids from the surgery covering their gloves. Screwdrivers and cobbs do not accurately take into account the geometry of the tulip head, thereby unable to efficiently provide an adequate hold on the tulip head for adjustment. Wrenches, particularly adjustable wrenches, are similar to plyers in that they provide an additional level of complexity during use, as well as requiring more time to adjust the wrench to an appropriate size for engaging the tulip head. Rongeurs require a significant amount of time to remove the bone, repeated insertions within the patient, and may not always give access to the bone on all sides of the tulip head. All the above tools involve factors that increase the risk of excessive damage and detrimental, long-term side effects for the patient. Certain of these tools may also result in damage to the pedicle screws.

Thus, there exists a need in the art for a system of acquiring access to a tulip head with minimal amount of tissue loss where surrounding tissue has grown around the tulip head. Additionally, a need exists for a tool designed to more efficiently and simply manipulate a tulip head in multiple directions while still being compatible with other instruments during surgery.

BRIEF SUMMARY OF THE INVENTION

The present disclosure is directed to a tulip rasp system and a tulip adjuster, and methods of using the same. The tulip rasp system permits a tulip head of a tulip screw to be access during revision spinal surgery. The tulip adjuster permits adjustment of the tulip head during various types of spinal surgery.

In one embodiment, a tulip rasp includes a body, a handle adjacent a proximal end of the body, a head adjacent a distal end of the body, the head having at least one extension, each of which has a cutting edge, and a receiving space defined by the at least one extension. Further, the tulip rasp may include a shaft received within the body and the receiving space. Further, the body may include a viewing space running along a portion of a length of the body. Further, the shaft may include a plurality of legs. Further, the head may include a first abrasive texture on an exterior surface on each of the at least one extension of the head. Further, the tulip rasp may include a sleeve extending over a portion of the body. Further, the sleeve may include a head received within the receiving space of the tulip rasp. Further, the tulip rasp may include wherein in a first position, there is a first distance between the plurality of legs, and, in a second position, there is a second distance between the plurality of legs, the first distance being greater than the second distance. Further, the tulip rasp may include an adjuster having a shaft defining a longitudinal axis and at least one extension extending from a distal end of the shaft of the adjuster at an angle transverse from the longitudinal axis. Further, the tulip rasp may include an end of the plurality of legs is bulbous in shape. Further, the tulip rasp may include a rasp guide having a rasp thread. Further, the adjuster may include a plurality of protrusions on the at least one extension. Further, the distal end of the at least one extension of the adjuster may have a first surface and a second surface, the first surface at a location proximal to the second surface. Further, the head may include a plurality of extensions.

In another embodiment, a method of using a tulip rasp comprises inserting the tulip rasp having a central passage to a first distance encapsulating a tulip head, rotating the tulip rasp about the tulip head to cut tissue with the edge within the central passage, and removing the tissue from within the central passage. Further, the method may include inserting an adjuster within the tulip head. Further, the method may include adjusting the tulip head with the adjuster. Further, the method may include inserting a rasp guide having a rasp thread within the central passageway to a second distance proximal to the tulip thread. Further, the method may include rotating the rasp guide to threadably engage rasp thread with a tulip thread of the tulip head. Further, the method include removing the tulip rasp and adjuster. Further, the method may include repeating the steps of inserting the tulip rasp, rotating the tulip rasp, and removing the tissue until an amount of tissue has been removed. Further, the method may include inserting a shaft having a plurality of legs within the central passageway. Further, the tulip rasp may comprise a viewing space, and the method further comprises viewing the viewing space to determine a visual indication of the first distance. Further, the method may include inserting a sleeve over a portion of the tulip rasp, and receiving a portion of the sleeve within the central passageway. Further, the method may include removing the shaft and creating a pressure within the central passageway.

In another embodiment, a method of using a tulip rasp comprising inserting the tulip rasp having a length to a first distance encapsulating a tulip head, rotating the tulip rasp about the tulip head to cut tissue with an edge of the tulip rasp, removing the tissue from within a central passage of the tulip rasp, inserting an adjuster within the tulip head, and adjusting the tulip head with the adjuster. Further, the method may include inserting a rasp guide having a rasp thread within the central passageway to a second distance proximal to the tulip thread. Further, the method may include rotating the rasp guide to threadably engage rasp thread with a tulip thread within the tulip head. Further, the method may include removing the tulip rasp, rasp guide, and adjuster. Further, the method may include repeating the steps of inserting the tulip rasp, rotating the tulip rasp, and removing the tissue until an amount of tissue has been removed. Further, the method may include inserting a shaft having a plurality of legs within the central passageway. Further, the tulip rasp may comprise a viewing space, and the method further comprises viewing the viewing space to determine a visual indication of the first distance. Further, the method may include inserting a sleeve over a portion of the tulip rasp, and receiving a portion of the sleeve within the central passageway. Further, the method may include removing the shaft and creating a pressure within the central passageway.

BRIEF DESCRIPTION OF THE DRAWINGS

These and other features, aspects, and advantages of the present invention will become better understood with regard to the following description, and accompanying drawings where.

DETAILED DESCRIPTION

As used herein, the words "proximal" and "distal," when used in connection with a medical device, refer to a position closer to and farther away from, respectively, a surgeon using the medical device. Thus, for example, the end of the medical device farthest from a surgeon would be the distal end of the medical device, while the end opposite the distal end and closest to a surgeon of the medical device, would be the proximal end of the medical device.

Figure 1:
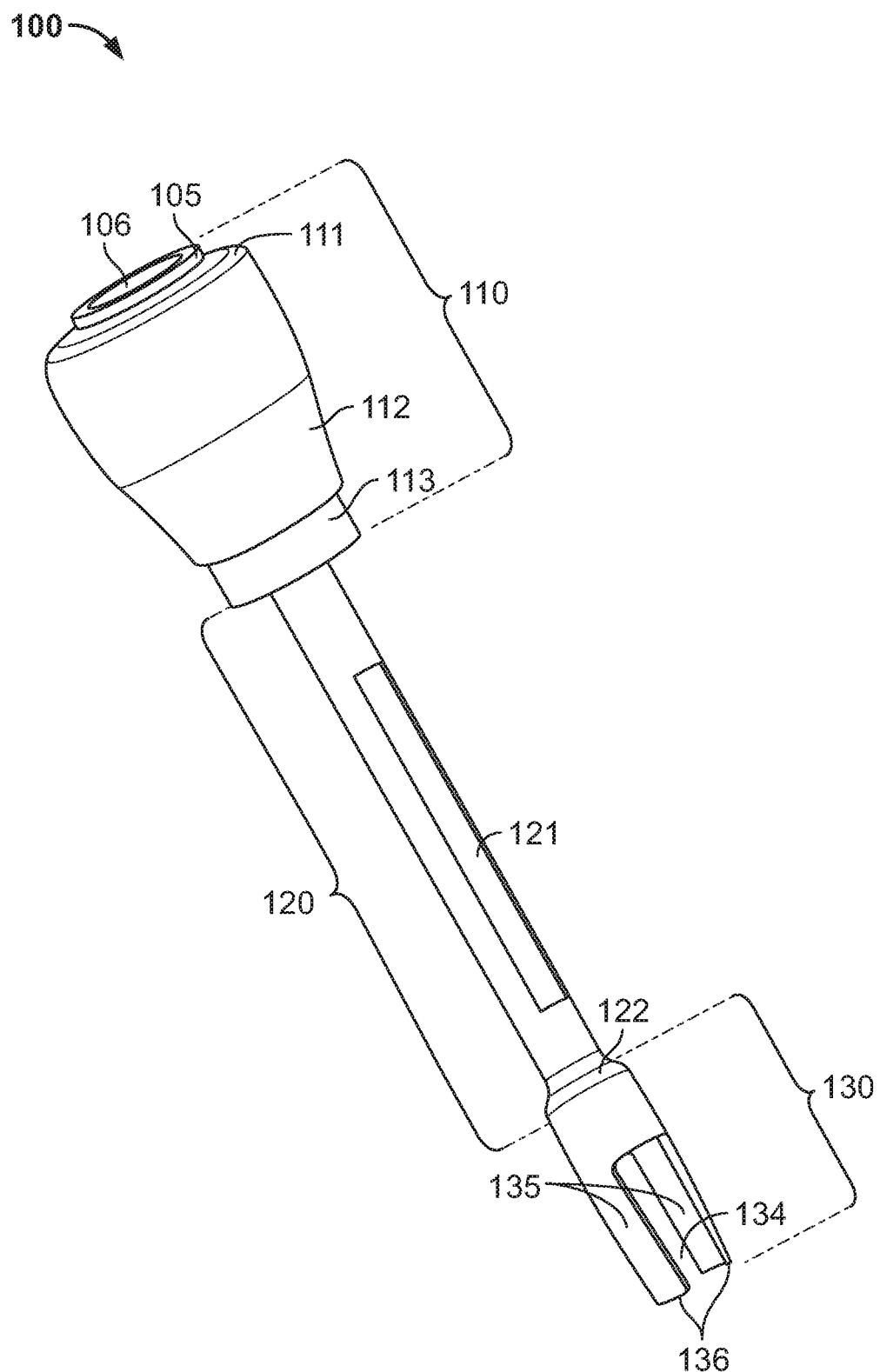
FIG. 1 depicts a perspective view of a tulip rasp according to one embodiment of the present invention.

In one embodiment of the invention, FIG. 1 depicts a tulip rasp 100 having a handle 110, body 120, and head 130 Handle 110 has chamfered portions 111 and 112 to allow for a surgeon to more comfortably grip tulip rasp 100. Proximal ledge 105 encircles proximal receiving space 106 to provide protection to handle 110 when inserting instruments within proximal receiving space 106. Distal ledge 113 is a thicker area surrounding body 120 and provides greater structural stability to tulip rasp system 100. Body 120 has a viewing space 121 to allow for the surgeon to visually confirm the depth of the instrument being inserted within tulip rasp system 100. Body chamfered portion 122 lies between body 120 and head 130, and is slanted such that, upon tulip rasp system being moved in a proximal direction, material pulled from within the surgery site may be minimized Head 130 has legs 135 with a smooth internal surface configured to receive a tulip head without deforming. Legs 135 are substantially rectangular with a thicker proximal portion tapering down to substantially linear edges 136. Edges 136 are designed to be sharp such that tulip rasp 100 may more easily and precisely be inserted over a tulip head, and have an abrasive texture to allow for greater bone removal.

Figure 2:
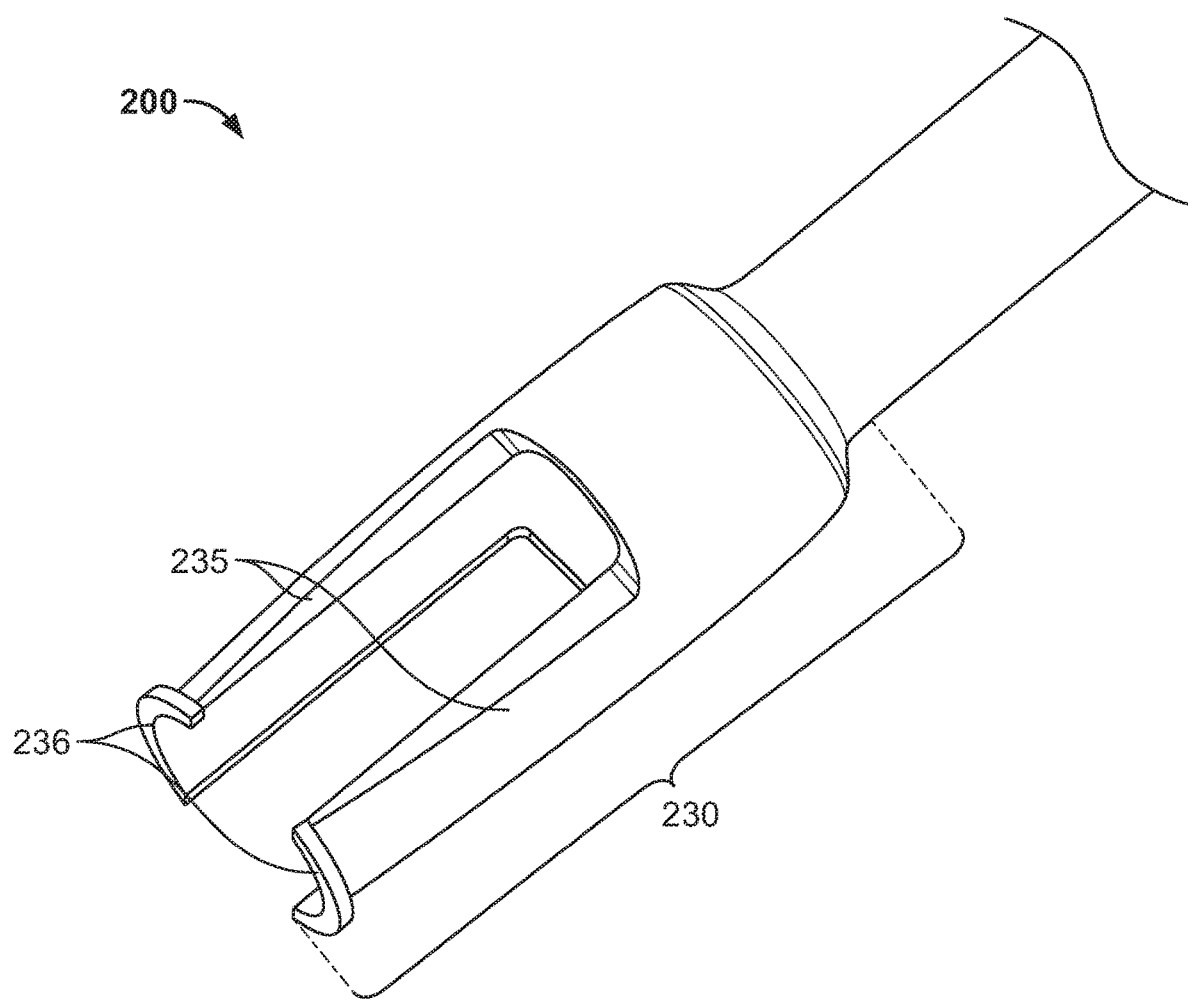
FIG. 2 depicts a partial view of the distal tip of a tulip rasp according to another embodiment of the invention.
Figure 3:
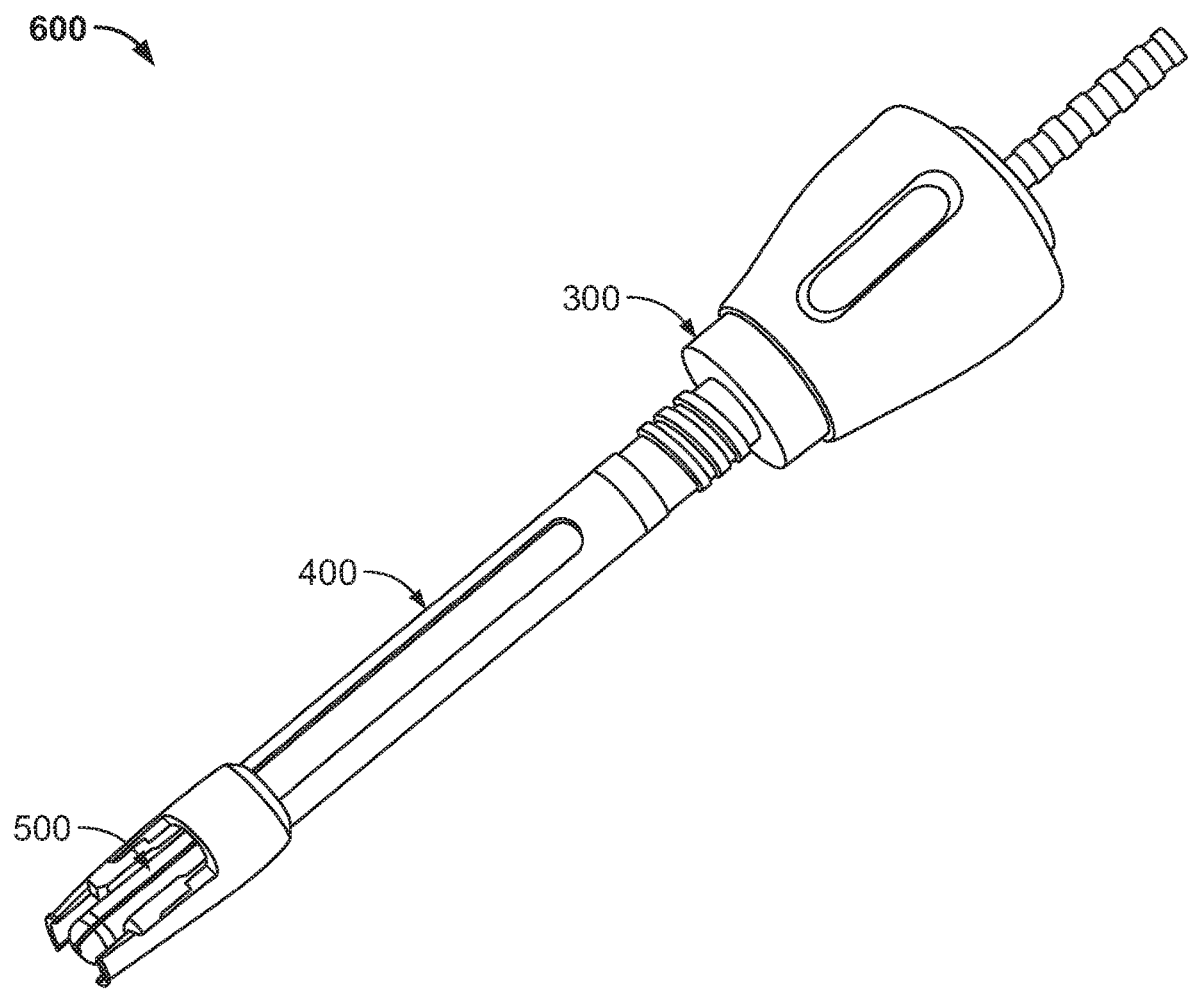
FIG. 3 depicts a perspective view of a tulip rasp system according to another embodiment of the present invention.
Figure 4:
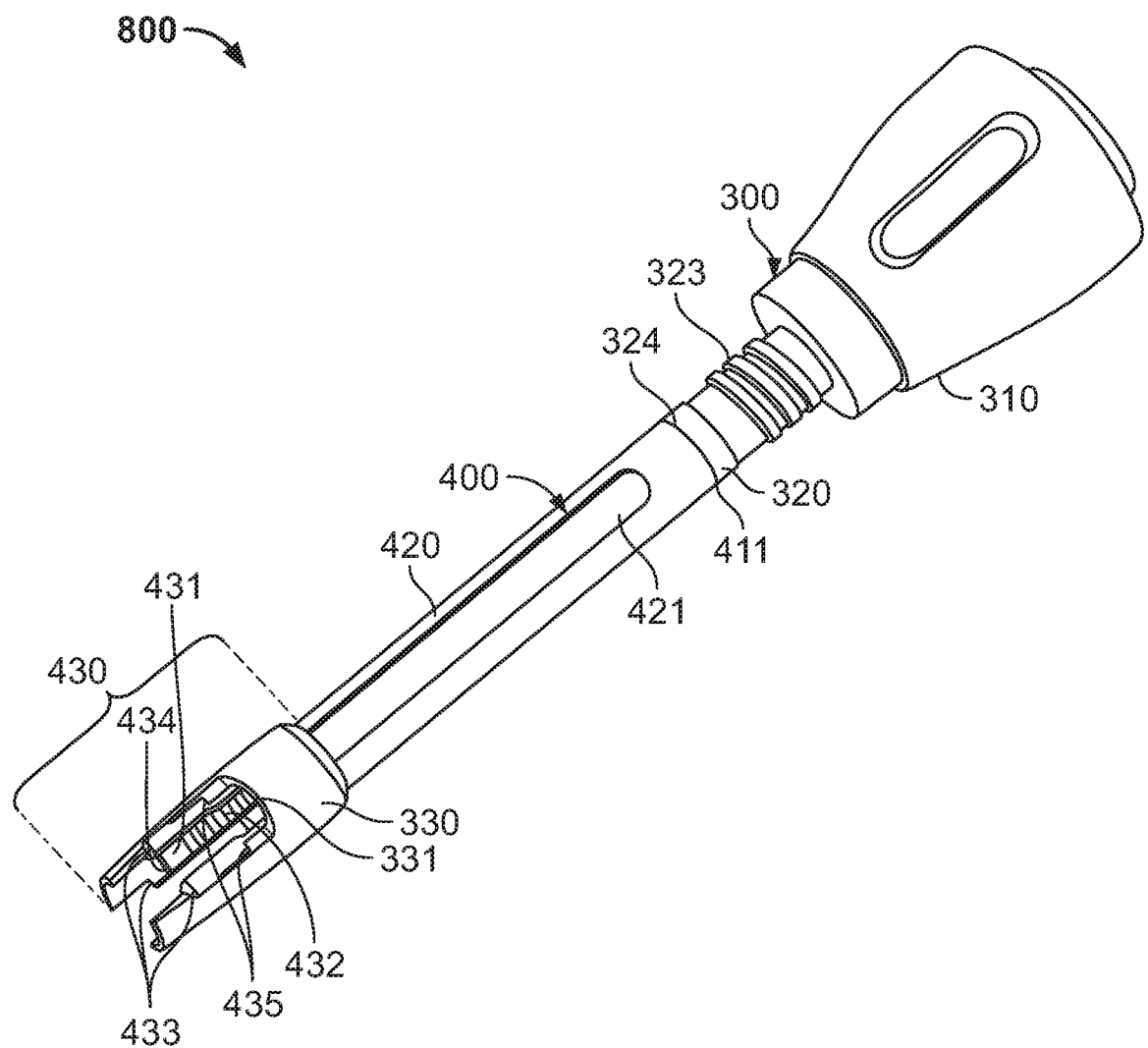
FIG. 4 depicts a perspective view of a tulip rasp and sleeve of tulip rasp system of FIG. 3.

Although FIG. 1 depicts tulip rasp 100 as having proximal ledge 105 and distal ledge 113, it is envisioned that, in other embodiments, there are no proximal and distal ledges. As shown in FIGS. 3-4 and described in greater detail, below, it is envisioned that there is no viewing space 121. In yet another embodiment, it is envisioned that there is no chamfered portions 111 and 112, and, instead, handle 110 includes a substantially geometric shape (e.g., a cylinder, rectangle, or the like). In yet another embodiment, head 130 may have an abrasive surface area on the exterior or interior of the head surface to further assist in removing tissue surrounding the tulip head. In yet another embodiment, it is envisioned that there may be any number of legs 135 (e.g., three legs). In yet another embodiment, it is envisioned that edges 136 is a non-linear shape (e.g., curved or zig-zagged). In yet another embodiment, it is envisioned that edges 136 may be one of sharp or abrasive. In another embodiment of the invention, FIG. 2 depicts tulip rasp 200 and head 230, as described above. In this embodiment, flanged edges 236 extend a distance from legs 235 and has an abrasive texture along the exterior surface to allow for greater bone removal. In this manner, not only would tulip rasp 200 assist in separating a tulip head from the surrounding tissue, but additional space can be provide such that the tulip head may be allowed to articulate, for instance, where the bone screw allows for polyaxial or uniaxial movement. Although flanged edges 236 protrude a distance from legs 235, they do not extend past the maximum circumference of the proximal portion of head 230. In this manner, where tulip rasp 200 is used in a minimally invasive manner, the risk of harm to the patient while tulip rasp 200 is being inserted into the working portal is minimized. It is also envisioned that tulip rasp 200 may be used in an open surgery, where such a risk is minimal.

In an embodiment of use, tulip rasp 100 may be used for a minimally invasive surgery or open surgery. For either forms of surgery, a surgeon may insert tulip rasp 100 in a distal direction towards a tulip head, as described in greater detail below, until the tulip head is received in distal receiving space 134. During or after the insertion, the surgeon may rotate handle 110 in a clockwise or counterclockwise direction until the tissue surrounding the tulip head has been removed. Where tulip rasp 100 is used for minimally invasive surgery, the surgeon may use viewing space 121 as a visual indication of the distance that head 130 has been inserted within the patient.

Figure 5:
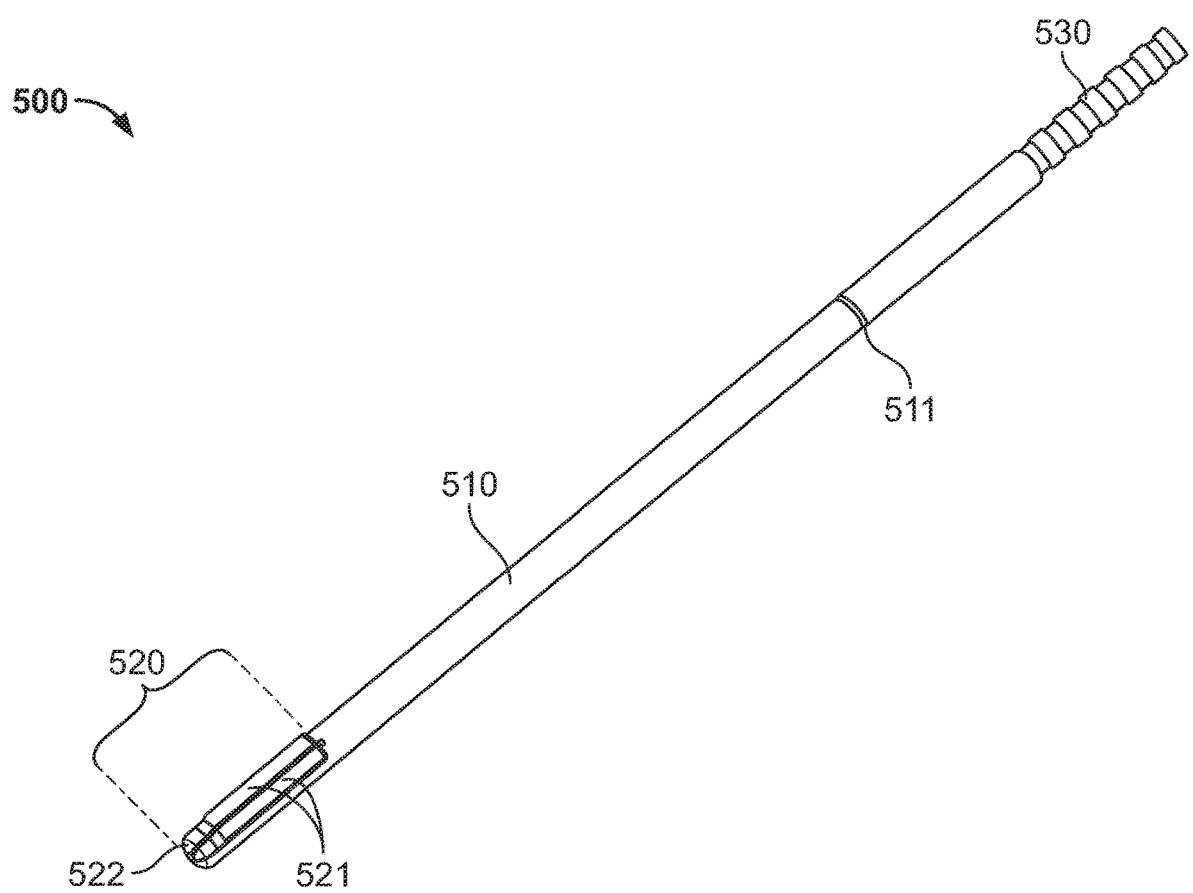
FIG. 5 depicts a perspective view of a shaft of tulip rasp system of FIG. 3.

FIGS. 3-5 depicts an embodiment of a tulip rasp system 600. FIG. 2 depicts tulip rasp system 600 including tulip rasp 300, sleeve 400, and shaft 500. Although tulip rasp system 800 is depicted as including sleeve 400, it is envisioned that other embodiments of a tulip rasp system may exclude sleeve 400.

FIG. 4 depicts tulip rasp 300 having a handle 310 and a head 330, as described above. In this embodiment, tulip rasp 300 includes a body 320 having a set of threads 323 distal of head 310. Threads 323 engage with an internal set of threads of sleeve 400 (not shown) such that tulip rasp 300 can be moved in a more controlled manner relative to sleeve 400. Although, body 320 does not have a viewing space, as shown in the tulip rasp embodiment of FIG. 1, it is envisioned that, in other embodiments, a tulip rasp may have both a viewing space and threads.

FIG. 4 also depicts sleeve 400. Sleeve 400 has a sleeve body 410 concentrically surrounding tulip rasp 300. Sleeve body 420 longitudinally extends from an end 411 through openings (not shown) in head 330 of tulip rasp 300 to sleeve legs 420 after tulip rasp 300 has been inserted over sleeve 400. Sleeve body 420 has sleeve viewing space 421 to allow for a surgeon to gauge the depth of sleeve 400 as sleeve 400 is being inserted within the patient. The inner surface of sleeve legs 430 include threads 432 and smooth portions 431, both of which are configured to receive instruments (e.g., alignment guides, retractors, compressors, distractors, or the like) for use in a revision surgery. A distal end of sleeve legs 430 is shaped to receive and contact a proximal surface of a tulip head, in use, through tips 433 and first surface 434. First surface 434 may contact the proximal surface of the tulip head while tips 433 engage the portions on either side of that proximal surface. Second surface 435 lies proximal to first surface 434 and tips 433, and is configured to contact head surface 331 and prevent further distal movement of tulip rasp 300. The length of sleeve legs 430 may be variable depending on the patient's anatomy and the size (and, specifically, the length) of the tulip head.

In other embodiments of the invention, it is envisioned that sleeve 400 does not have tips 433 and first surface 434 is the most distal portion of sleeve 400. It yet another embodiment of the invention, it is envisioned that sleeve body 420 has no viewing portal 421. It yet another embodiment of the invention, it is envisioned that the internal surface of sleeve legs 430 is composed entirely if smooth portion 431 or threads 432. In yet another embodiment of the invention, handle 310 has an opening (not shown) for sleeve 400 to be received in. In this manner, threads 323 may rotatably engage the internal threads of sleeve 400 when sleeve 400 is inserted distally through handle 310 or tulip rasp 300 is moved proximally relative to sleeve 400. In yet another embodiment, a proximal end 411 of sleeve 400 abuts against surface 324 preventing tulip rasp 300 from moving further in a distal direction. This abutment may be in addition to, or in lieu of, the contact between second surface 435 and head surface 331 in preventing further distal movement of tulip rasp 300. In yet another embodiment, the distal end of sleeve legs 430 is a smooth surface without tips 433.

In a method of use, tulip rasp 300 and sleeve 400 may already be coupled together, as shown in tulip rasp system 800 of FIG. 4. In this embodiment, tulip rasp system 800 is inserted until tips 433 and first surface 434 contact and engage a proximal surface of a tulip head, preventing any further insertion of sleeve 400. Tulip rasp 300 is further inserted until threads 323 rotatably engage an internal set of threads within sleeve 400. Through this engagement, tulip rasp 300 may continue to be inserted in a controlled manner by rotating tulip rasp 300 until head surface 331 contacts second surface 435, thus preventing tulip rasp 300 from being inserted too far within the patient. Once tulip rasp 300 has reached a desired depth, further rotation of tulip rasp 300 rotates sleeve 400 through the contact between the openings of head 330 and sleeve 400 which, in turn, rotates the tulip head through the engagement of the distal end of sleeve legs 433 and the tulip head. The surgeon may continue rotating tulip rasp system 800 until the tulip head is freed from the surrounding bone and tissue overgrowth.

Figure 6:
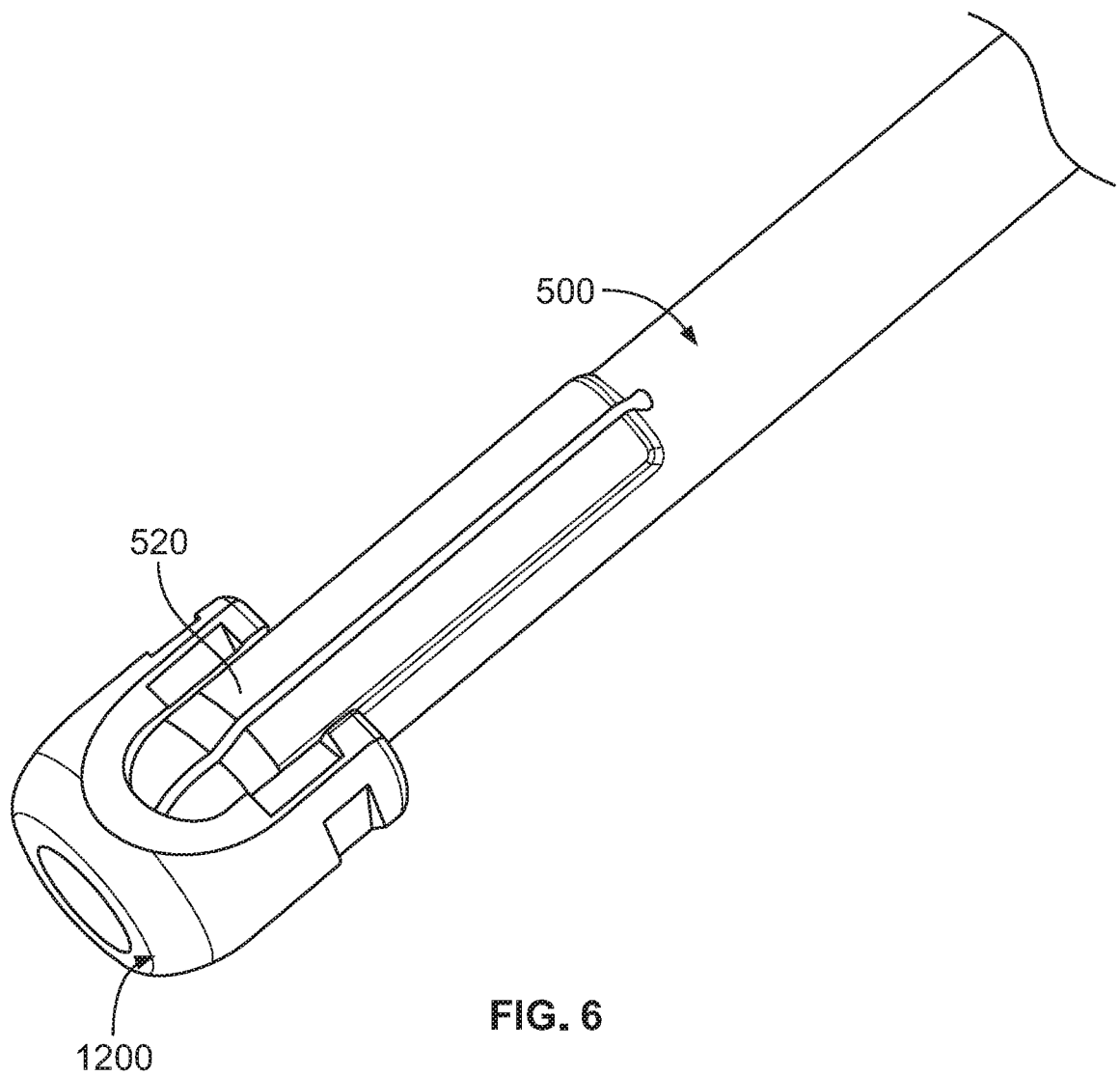
FIG. 6 depicts a partial view of the shaft of tulip rasp system of FIG. 3 in use with a tulip head of a pedicle screw according to another embodiment of the present invention.

In an alternative method of use, it is envisioned that second surface 435 is already in contact with head surface 331 prior to insertion and tulip rasp system 800 is inserted until the distal end of legs 430 engage with the proximal surface of the tulip head. In yet another embodiment, it is envisioned that sleeve legs 430 do not have tips 433 such that the distal end of sleeve legs 430 contacts, but does not engage, the proximal surface of the tulip head. In yet another embodiment, tulip rasp 300 may be used without sleeve 400. FIG. 5 depicts shaft 500 having a shaft body 510, shaft legs 520, and section 530. Shaft 500 may act, in part, as a centering mechanism to align other instruments to be inserted over shaft 500 during surgery. Shaft body 510 is substantially cylindrical and extends from a proximal end of shaft legs 520 and distal end of section 530. Shaft body 510 has a marker 511 that provides a visual indication to the surgeon of how far shaft 500 has been inserted. Shaft legs 520 includes shaft portions 521 and shaft tips 522. Shaft portions 521 protrudes a distance from shaft legs 520 along at least a portion thereof and has a combined width to insert into a slot of tulip head 1200, as shown in FIG. 6, below. The proximal and distal ends of shaft portions 521 are chamfered to support insertion into a variety of screw types, such as an angled screw or the like. Shaft tips 522 is a bulb gasket that, upon shaft 500 being pulled out of the patient's body, creates a negative pressure that can act as a suction mechanism to assist in removing residual tissue from within the working portal of the patient's body. As with the chamfered portions of shaft portions 521, the round shape of shaft tips 522 assists in inserting shaft 500 into a screw that has been angled in situ by allowing shaft 500 to more easily slide into, and coaxially align with, the tulip head. Section 530 has a number of circumferential indentations to provide the surgeon a better grip when pulling shaft 500 out of the patient, although other types of grip surfaces are envisioned (e.g., longitudinal ribs or the like).

In other embodiments of the invention, it is envisioned that shaft tips 522 is not bulbous and has an alternative shape (e.g., having one or more sharp corners or a substantially linearly tapering down to a point). In yet another embodiment of the invention, it is envisioned that shaft legs 520 does not have shaft portions 521 and, instead, have a substantially smooth exterior surface. It yet another embodiment of the invention, it is envisioned that shaft body 510 does not have marker 511. It yet another embodiment of the invention, it is envisioned that the grip provided by section 530 may be provided an alternative means (e.g., protruding ridges or a handle mechanism).

Figure 7:
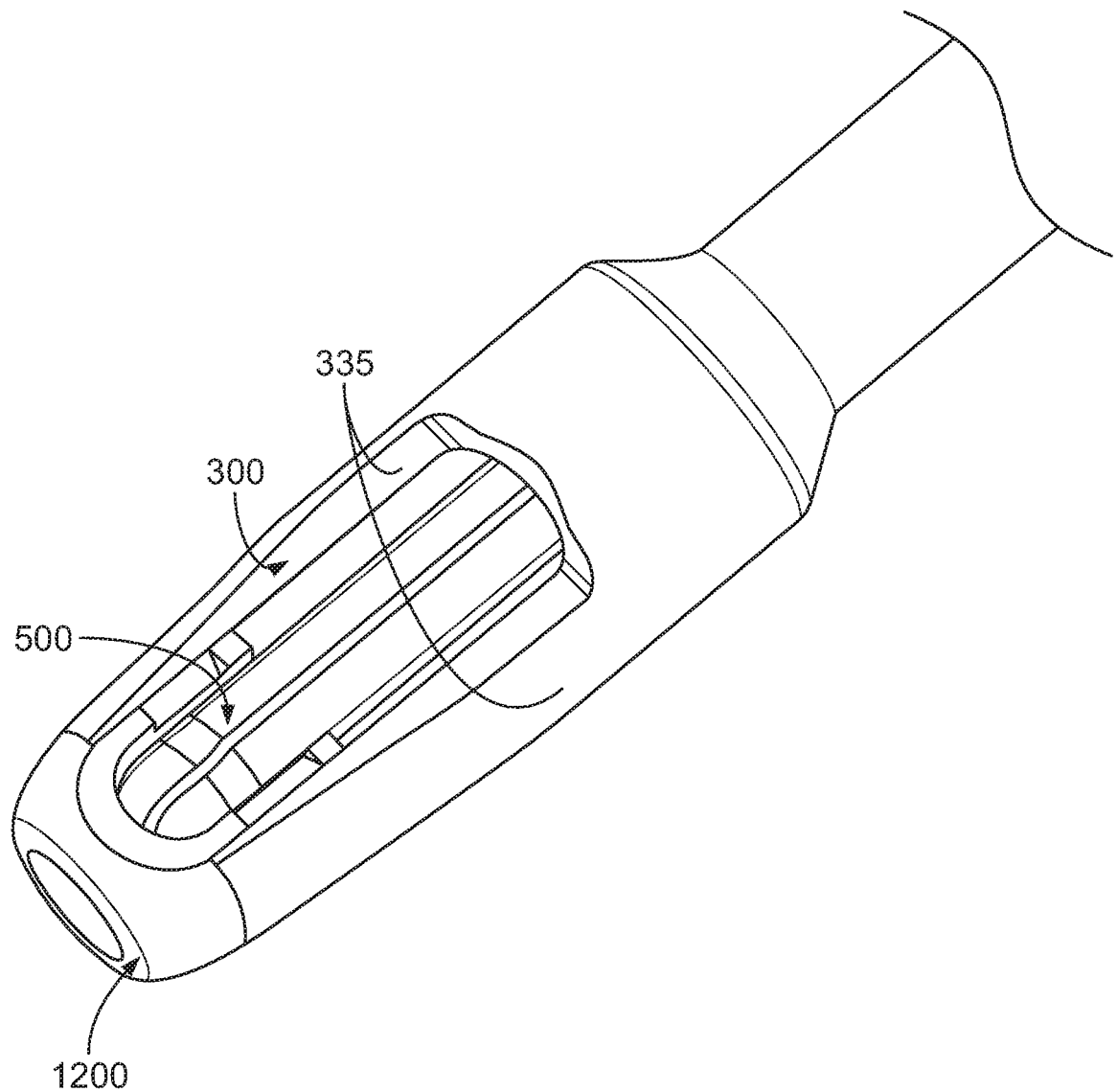
FIG. 7 depicts a partial view of the shaft and tulip rasp of tulip rasp system of FIG. 3 in use with a tulip head of a pedicle screw according to another embodiment of the present invention.

FIGS. 6-7 depicts an embodiment of use of tulip rasp system 600, as described in FIGS. 3-5, above. It is envisioned that tulip rasp system 600 may be used for both minimally invasive surgery and open surgery. Where tulip rasp system 600 is used for minimally invasive surgery, a small incision is made on the body of a patient (not shown). FIG. 6 shows where shaft legs 520 of shaft 500 is inserted within tulip head 1200, allowing for the proper alignment of other instruments that may be slid over shaft 600 during surgery. During insertion, shaft legs 520 inwardly flex to create a tight fit within tulip head 1200 such that, when shaft 500 is pulled out, shaft legs 520 expands to create a negative pressure; thus, providing greater removal of debris within tulip head 1200. FIG. 7 shows where tulip rasp 300 is slid or rotated over shaft 500 such that legs 335 encapsulate at least a portion of tulip head 1200. Although not shown in FIGS. 6-7, other embodiments of use envision that sleeve 400 may optionally be inserted over shaft 600 prior to, or in conjunction with, tulip rasp 300 to prevent tulip rasp 300 from overextending into the patient.

Once a desired depth has been reached, tulip rasp 300 may be rotated about a longitudinal axis defined by tulip rasp 300 to separate tulip head 1200 from surrounding tissue overgrowth by, for instance, a surgeon twisting handle 310 in a clockwise or counter-clockwise direction. Once tulip head 1200 has been sufficiently freed from the surround tissue, tulip rasp system 800 may be removed from within the patient. At this point, shaft 500 may be pulled out to remove excess tissue from within the opening of the tulip head 1200. Shaft 500 may be pulled out first to allow for tulip rasp system 800 to maintain engagement with tulip head 1200 while allowing for other instruments to be inserted within tulip rasp system 600 and into tulip head 1200, or from an alternate angle outside tulip rasp system 600, such as with a tulip adjuster, as further described in FIGS. 9-11, below.

Figure 8:
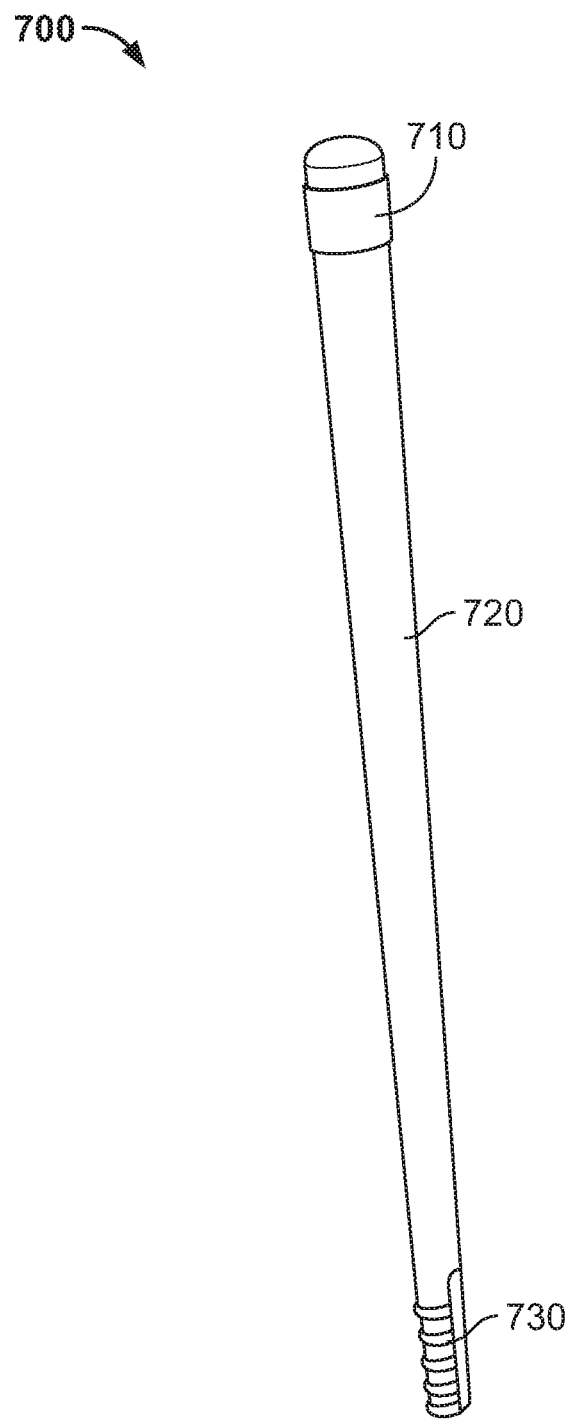
FIG. 8 depicts a rasp guide according to another embodiment of the invention.

In another embodiment of the invention, FIG. 8 depicts rasp guide 700 having proximal head 710, shaft 720, and thread 730. Similar to shaft 500, as described above, rasp guide 700 may act as a centering mechanism to align other instruments to be inserted over rasp guide 700. Proximal head 710 has a greater diameter than shaft 720 allowing for a better grip when held by a surgeon. Further, the proximal end of rasp guide 700 tapers from the diameter of proximal head 710 to a smaller diameter of thread 730. Thread 730 is designed to be engaged with an internal threading (not shown) of a tulip head 1200.

Although FIG. 8 depicts rasp guide 700 having proximal head 710, it is envisioned, in other embodiments, that there is no proximal head 710. In yet another embodiment, it is envisioned that there is no taper and the diameter of rasp guide 700 remains substantially similar throughout its length. In yet another embodiment, proximal head 710 may have a non-cylindrical surface (e.g. hexagonal, rectangular, or the like) for greater ease of use by an operator or for use in conjunction with other tools. In yet another embodiment, proximal head 710 may run at least half the length of shaft 720.

In another embodiment of use, rasp guide 700 may be used with tulip rasp 300, and optionally sleeve 400, as described above. Similar to shaft 500, rasp guide 700 may be inserted within a patient and threadably engage a tulip head such that other instruments may be inserted over rasp guide 700 to interact with the tulip head in an aligned manner Tulip rasp 300 and sleeve 400 may be used, as described above. Rasp guide 700 may then be retrieved from within the patient. While rasp guide 700 does not have the suction capabilities of shaft 600 to assist in removing excess tissue, the attachment between rasp guide 700 and the tulip head is more secure, allowing for greater control and precision of alignment.

Figures 9A, 9B:
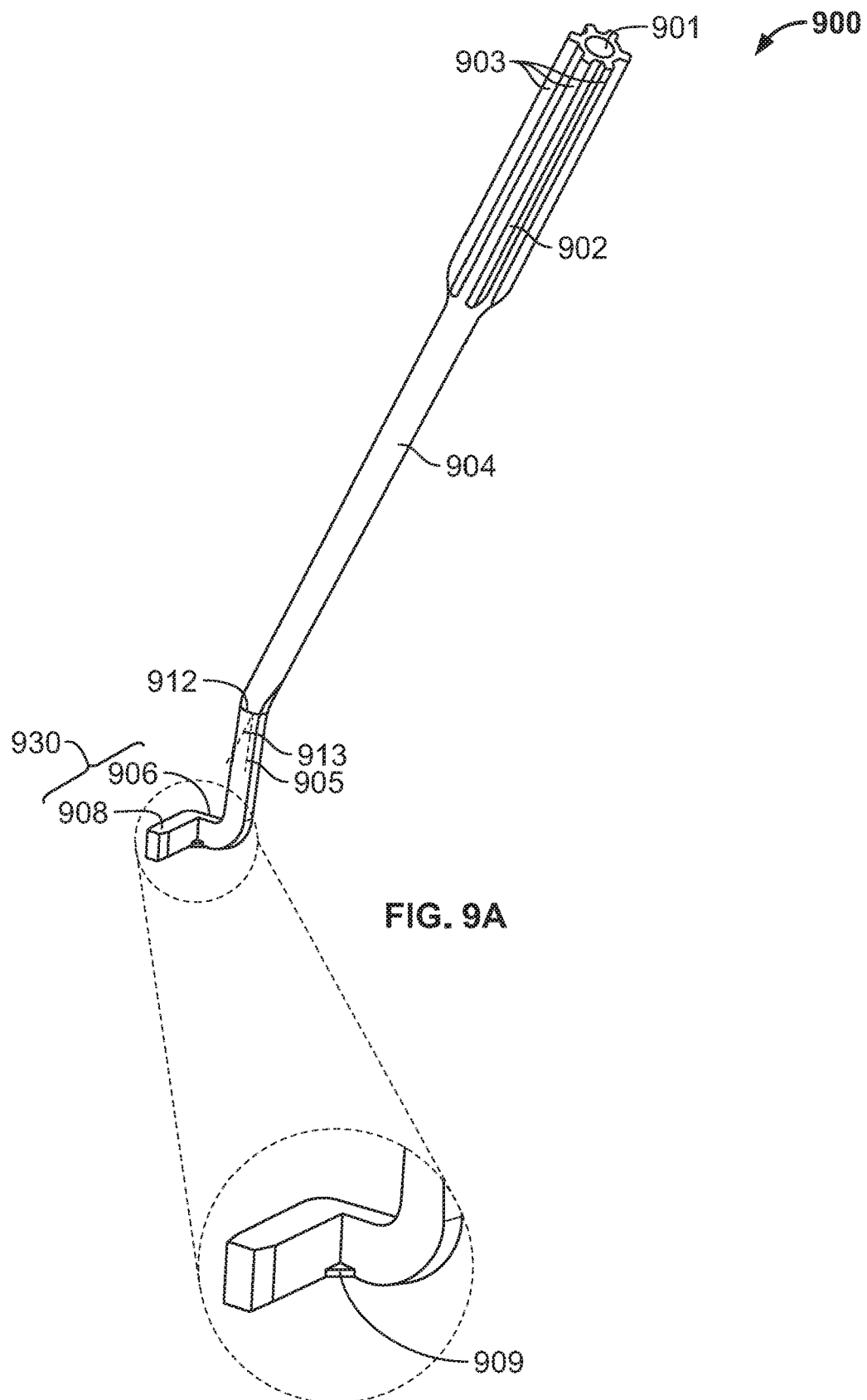
FIG. 9A depicts a perspective view of a tulip adjuster according to another embodiment of the present invention.
FIG. 9B depicts a partial view of the distal tip of the tulip adjuster of FIG. 9A.

In another embodiment of the invention, FIGS. 9A-B depicts tulip adjuster 900 having an adjuster handle 902, shaft 904, and adjuster head 930. Adjuster handle 902 has a longitudinal axis and handle protrusions 903 running the length of adjuster handle 902. Protrusions 903 are rounded to provide increased grip for an operator. Tulip adjuster 900 defines a space 901 through handle 902 such that the weight of tulip adjuster 900 is reduced and allowing for tulip adjuster 900 to be more easily handled by a surgeon. Shaft 904 from handle 902 extends distally along the longitudinal axis until point 912, where angled shaft portion 905 extends distally at an angle 913 from the longitudinal axis. Adjuster head 930 has first shaft portion 906 extending at a right angle from angled shaft portion 905 and second shaft portion 908 extending at a right angle from first shaft portion 906. Buffer 909 sits at the corner between first shaft portion 908 and second shaft portion 907. Buffer 909 is a triangular block of material on the corner between first shaft portion 906 and second shaft portion 908 prevents. Buffer 909 assists tulip adjuster 900 from getting caught on a tulip head (not shown) during use by preventing the corner and the tulip head from being in direct contact. Although FIG. 9B depicts the distal end of adjuster head 930 as having a chamfered end, it is envisioned that, in other embodiments, the end may be any shape, including rounded. In yet another embodiment, handle protrusions may be rectangular. In year another embodiment, there may be no handle protrusions.

Figure 10:
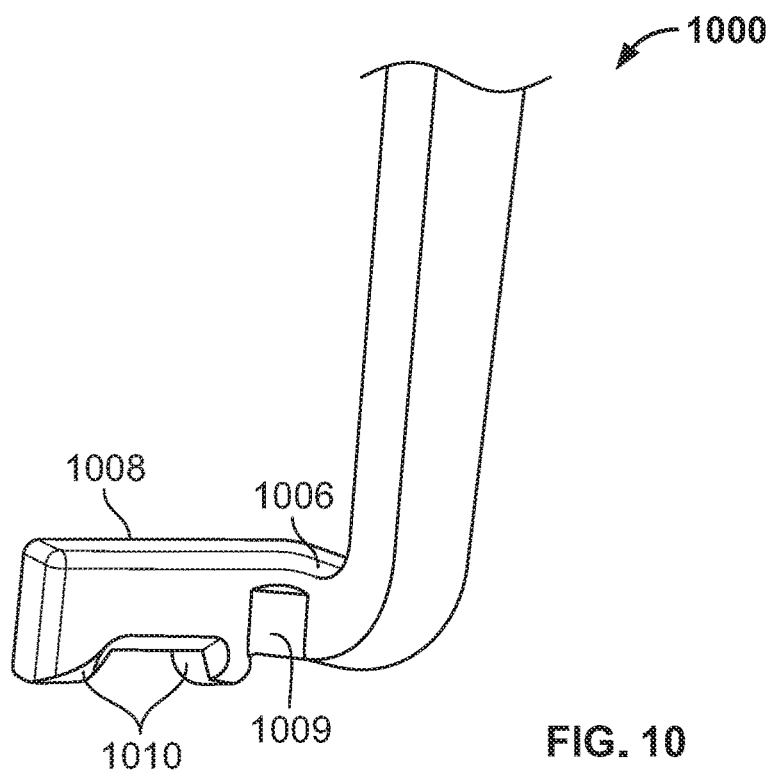
FIG. 10 depicts a partial view of a distal tip of a tulip adjuster according to another embodiment of the present invention.
Figure 12:
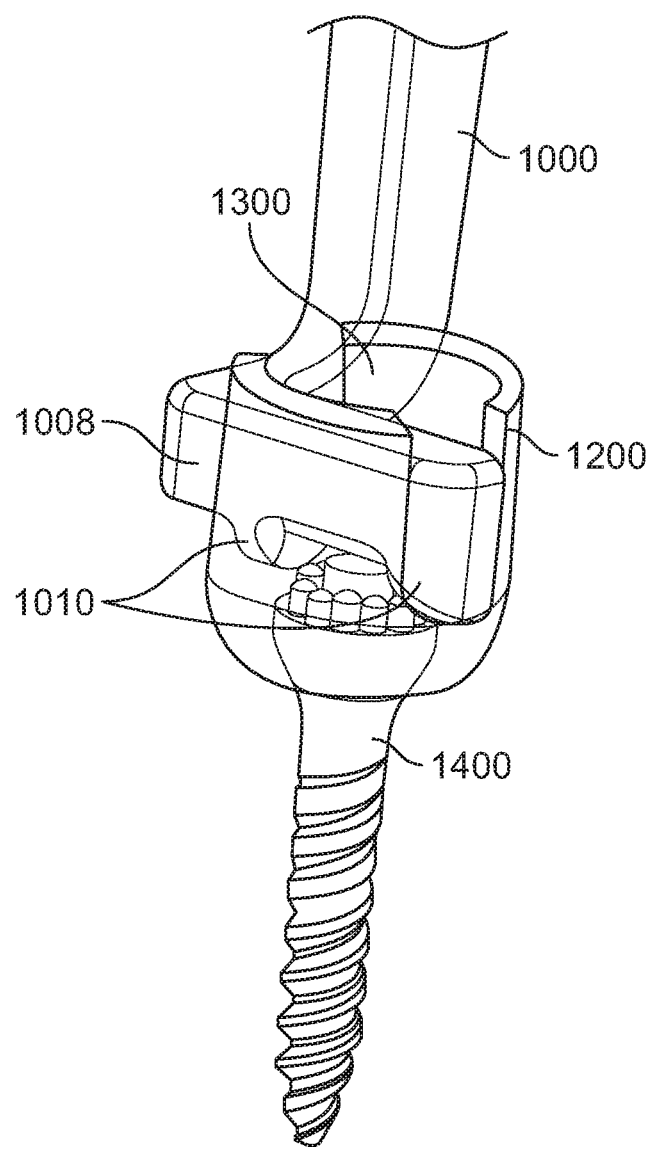
FIG. 12 depicts a partial view of a distal tip of a tulip adjuster in use with a tulip head and tulip screw according to another embodiment of the present invention.

In another embodiment of the invention, FIG. 10 depicts a partial view of the distal end of tulip adjuster 1000 having first shaft portion 1006, second shaft portion 1008, and buffer 1009, as described above. In this embodiment, tulip adjuster 1000 has two protrusions 1010 extending from the distal surface of second shaft portion 1008. Protrusions 1010 are configured to engage with the exterior surface of tulip head 1200 after tulip adjuster 900 has been inserted into tulip receiving space 1300, as shown in FIG. 12. In this manner, tulip adjuster 1000 may provide greater control when a surgeon is adjusting tulip head 1200 with tulip adjuster 1000, as described in greater detail below. Although FIG. 10 depicts protrusions 1010 as rounded, it is envisioned that, in other embodiments, protrusions 1010 may be any shape, including chamfered or squared.

Figure 11:
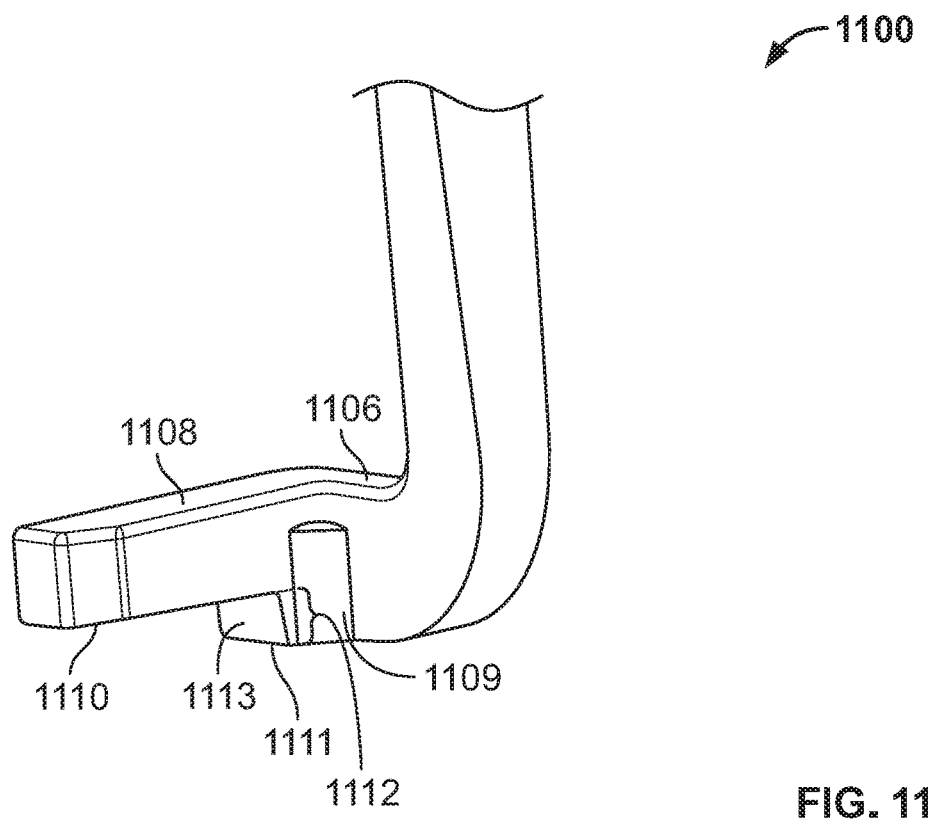
FIG. 11 depicts a partial view of a distal tip of a tulip adjuster according to another embodiment of the present invention.

In another embodiment of the invention, FIG. 11 depicts a partial view of the distal end of tulip adjuster 1100 having first shaft portion 1106, second shaft portion 1108, and buffer 1109, as described above. In this embodiment, first surface 1110 of second shaft portion 1108 is at a distance 1112 proximal from second surface 1111. When tulip adjuster 1100 is inserted into within a tulip receiving space of a tulip head (not shown), third surface 1113 is in contact with an exterior portion of the tulip head 1200. In this manner, tulip adjuster 1100 may provide greater control when an operator is adjusting the tulip head with tulip adjuster 1100.

In one embodiment of the invention, FIG. 12 depicts a perspective view of tulip 1000 in use with tulip head 1200, as described above. Second shaft portion 1008 is inserted within tulip receiving portion 1300 such that protrusions 1010 sit on an exterior surface of tulip head 1200. In this manner, the operator may shift the angle of orientation between tulip head 1200 and tulip screw 1400 to a desired position by maneuvering adjuster 1000 while minimizing the risk of second shaft portion 1008 sliding out of tulip receiving portion 1300.

In addition to that described above and illustrated in the figures, various other operations will now be described. It should be understood that the following operations do not have to be performed in the exact order described below. Instead, various steps may be handled in a different order or simultaneously. Steps may also be omitted or added unless otherwise stated therein.

In another embodiment of use, tulip rasp system 200 and tulip adjuster 1000 may be used in conjunction to adjust a tulip head. After the tissue surrounding the tulip head has been cleared, and the surgeon has retrieved shaft 500 or rasp guide 700, as described above, tulip adjuster 1000 is inserted within the tulip head until protrusions 1010 lie flush along the exterior of the tulip head. The surgeon then adjusts the tulip head to a desired orientation is reached. The surgeon removes tulip adjuster 1000 from the incision. Alternatively, it is envisioned that tulip adjuster 1000 may be used to adjust a tulip head separately from any tulip rasp system. For instance, where access to the tulip head has been acquired by some other means (e.g. in an open surgery, or with another tool), the tulip adjuster may be used in a similar manner as described above. Moreover, tulip adjuster 1000 may have applicability to initial (i.e., non-revision) surgeries to aid in the positioning of tulip heads with respect to spinal rods or other components. In yet another embodiment of use, it is envisioned that both rasp guide 700 and shaft 500 may both be used in the surgery. For instance, where tissue has infiltrated a tulip head such that the interior of the tulip head is inaccessible except for a portion of the tulip head's internal threads, a surgeon may have difficulty using shaft 500 to center the tulip head. In this instance, rasp guide 700 may be used to center the tulip head by potentially securing at least a portion of threads 730 to any exposed threads of the tulip head. The tissue and bone surrounding the tulip head may then be removed as described above. Once the tulip head has been freed and rasp guide 700 has been removed from the patient, the surgeon may then use the suction mechanism provided by shaft 500 to remove excess tissue remaining within the tulip head.

Where tulip rasp system 200 is used for open surgery, the tissue surrounding the tulip head is exposed. Tulip rasp system 200 is inserted over the tulip head 1100 to remove tissue surrounding the tulip head, as described above. In this embodiment of use, rasp guide 700 and shaft 500 are optional as an open surgery allows easier access to the tulip head without requiring either rasp guide 700 or shaft 500 for centering and alignment. While shaft 500 is optional in this embodiment of use, there may be benefits to using shaft 600 for the purposes of removing excess tissue from within the opening of the tulip head. Tulip adjuster 1000 is then inserted within the tulip head until protrusions 1010 lie flush along the exterior of the tulip head. The surgeon then adjusts the tulip head until a desired orientation is reached. The operator removes tulip adjuster 1000 from the incision. The operator then continues with performing any subsequent steps of the surgery, including removing tulip rasp system 200 from around the tulip head or inserting rasp guide 700 or shaft 600 into the tulip head.

In other embodiments, it is envisioned that no rasp guide is used. In yet another embodiment, it is envisioned that rasp guide 700 is inserted before inserting the tulip rasp system. In yet another embodiment, it is envisioned that any embodiment of tulip adjusters, as shown in FIGS. 9-11, any embodiment of tulip rasps, as shown in FIGS. 1-2, and any embodiment of tulip rasp systems, as shown in FIG. 3, may be used in a minimally invasive surgery or open surgery.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A tulip rasp system comprising:
   a tulip head;
   a tulip rasp: comprising:
      a body;
      a handle adjacent a proximal end of the body;
      a head adjacent a distal end of the body, the head having at least one substantially rectangular extension that tapers down to a substantially linear cutting edge; and
      a receiving space defined by the at least one extension for receiving at least a portion of the tulip head; and
   an adjuster for shifting an angle of orientation of the tulip head, the adjuster having an adjuster shaft defining a longitudinal axis, a first extension extending from a distal end of the adjuster shaft at a first angle transverse to the longitudinal axis, and a second extension extending from the first extension at a second angle transverse to the first extension, at least one of the first and second extensions at least partially insertable laterally through the tulip rasp and a sidewall of the tulip head while the tulip head is received within the receiving space of the tulip rasp.

2. The tulip rasp system of claim 1, further comprising a shaft received within the body and the receiving space.

3. The tulip rasp system of claim 1, wherein the body further comprises a viewing space running along a portion of a length of the body.

4. The tulip rasp system of claim 2, wherein the shaft includes a plurality of legs.

5. The tulip rasp system of claim 1, wherein the head further comprises a first abrasive texture on an exterior surface on each of the at least one extension of the head.

6. The tulip rasp system of claim 1, further comprising a sleeve extending over a portion of the body.

7. The tulip rasp system of claim 6, wherein the sleeve includes a head received within the receiving space of the tulip rasp.

8. The tulip rasp system of claim 4, wherein in a first position, there is a first distance between the plurality of legs, and, in a second position, there is a second distance between the plurality of legs, the first distance being greater than the second distance.

9. The tulip rasp system of claim 4, wherein an end of the plurality of legs is bulbous in shape.

10. The tulip rasp system of claim 1, further comprising a rasp guide having a rasp thread.

11. The tulip rasp system of claim 1, wherein the adjuster has a plurality of protrusions on the second extension.

12. The tulip rasp system of claim 1, wherein a distal end of the second extension of the adjuster has a first surface and a second surface, the first surface at a location proximal to the second surface.

13. The tulip rasp system of claim 1, wherein the head comprises a plurality of extensions.

14. A method of using a tulip rasp system comprising:
   inserting a tulip rasp having a body, a handle, a head, a central passage, and a receiving space defined by at least one substantially rectangular extension of the head to a first distance encapsulating a tulip head within the receiving space;

rotating the tulip rasp about the tulip head to cut tissue with a substantially linear cutting edge to which the at least one substantially rectangular extension tapers down;

laterally inserting a distal end of an adjuster through the tulip rasp and a sidewall of the tulip head while the tulip head is encapsulated within the receiving space of the tulip rasp;

manipulating the adjuster to shift an angle of orientation of the tulip head, wherein the distal end of the adjuster comprises a first extension extending from a distal end of an adjuster shaft of the adjuster at a first angle transverse to a longitudinal axis of the adjuster shaft and a second extension extending from the first extension at a second angle transverse to the first extension; and removing the tissue from within the central passage.

15. The method of claim 14, further comprising inserting a rasp guide having a rasp thread within the central passage to a second distance proximal to the tulip head.

16. The method of claim 15, further comprising rotating the rasp guide to threadably engage the rasp thread with a tulip thread of the tulip head.

17. The method of claim 16, further comprising removing the tulip rasp and the adjuster.

18. The method of claim 14, further comprising repeating the steps of inserting the tulip rasp, rotating the tulip rasp, and removing the tissue until an amount of tissue has been removed.

19. The method of claim 14, further comprising inserting a shaft having a plurality of legs within the central passage.

20. The method of claim 19, further comprising removing the shaft and creating a pressure within the central passage.

21. The method of claim 14, wherein the tulip rasp further comprises a viewing space, and the method further comprises viewing the viewing space to determine a visual indication of the first distance.

22. The method of claim 14, further comprising inserting a sleeve over a portion of the tulip rasp, and receiving a portion of the sleeve within the receiving space.

\* \* \* \* \*